(12) United States Patent
Harris et al.

(10) Patent No.: US 6,466,319 B2
(45) Date of Patent: Oct. 15, 2002

(54) METHOD AND APPARATUS FOR DETERMINING THE DISPERSION STABILITY OF A LIQUID SUSPENSION

(75) Inventors: Jerome Michael Harris, Penllyn, PA (US); Daniel Alain Saucy, Harleysville, PA (US)

(73) Assignee: Rohm and Haas Company, Philadelphia, PA (US)

( * ) Notice: Subject to any disclaimer, the term of this patent is extended or adjusted under 35 U.S.C. 154(b) by 64 days.

(21) Appl. No.: 09/820,409

(22) Filed: Mar. 29, 2001

(65) Prior Publication Data

US 2001/0046048 A1 Nov. 29, 2001

Related U.S. Application Data

(60) Provisional application No. 60/195,736, filed on Apr. 7, 2000.

(51) Int. Cl.$^7$ .......................... G01N 21/00; G01N 15/02
(52) U.S. Cl. ........................................ 356/338; 356/336
(58) Field of Search ................................. 356/336, 337, 356/338, 341; 250/574

(56) References Cited

U.S. PATENT DOCUMENTS

| | | | | |
|---|---|---|---|---|
| 4,348,111 A | * | 9/1982 | Goulas et al. | 356/336 |
| 4,940,900 A | | 7/1990 | Lambert | 250/343 |
| 5,063,301 A | | 11/1991 | Turkevich et al. | 250/574 |
| 5,194,921 A | | 3/1993 | Tambo et al. | 356/432 |
| 5,506,673 A | * | 4/1996 | Kosaka et al. | 356/336 |
| 5,620,609 A | | 4/1997 | Field | 210/745 |
| 5,783,826 A | | 7/1998 | Meunier | 250/341.8 |
| 5,912,257 A | * | 6/1999 | Prasad et al. | 250/338.1 |
| 6,311,550 B1 | * | 11/2001 | Lehmikangas et al. | 356/338 |
| 6,369,890 B1 | * | 4/2002 | Harley | 250/574 |
| 6,417,920 B1 | * | 7/2002 | Shimaoka | 356/336 |
| 2002/0036776 A1 | * | 3/2002 | Shimaoka | 356/336 |
| 2002/0044281 A1 | * | 4/2002 | Sakamoto et al. | 356/336 |

FOREIGN PATENT DOCUMENTS

EP 0947822 10/1999

OTHER PUBLICATIONS

Chen, M., et al, "Characteristics of Flocculated Silica Dispersions", Journal of Colloid and Interface Science, vol. 141, No. 2, Feb. 1991.
Scarpello, Justin T., et al, "The influence of system parameters on the stability of colloidal liquid aphrons", Society of Chemical Industry, 1999, J. Chem. Technol Biotechnol, 0268–2575/99.
Maver, Tammy L, "Rheology Modifiers: Modeling Their Performance in High Gloss Paints", Journal of Coatings Technology. vol. 64, (812) 45–58, Sep. 1992.
Mengual, O, Characterisation of Instability of Concentrated Dispersions by a New Optical Analyzer: the TURSIBCAN MA 1000, Colloids and Surfaces A: Physicochemical and Engineering Aspects 152 (1999) 111–123.
"A New Concept in Colloidal Analysts"., Coulter Quick-SCANυ, 1997.

* cited by examiner

*Primary Examiner*—Ricky Mack

(57) ABSTRACT

The present invention relates to a method and apparatus for determining the dispersion stability of a liquid suspension. The method of the present invention includes exposing the liquid suspension to one or more appropriate wavelengths of light while maintaining insoluble particles in the liquid suspension uniformly suspended, and determining the amount of light scattered by the liquid suspension to assess the dispersion stability of the liquid suspension. The present invention also provides an apparatus for carrying out the method of the present invention. The method and apparatus of the present invention can be used, for example, to determine the effect that an additive has on the dispersion stability of a liquid suspension without having to wait for the liquid suspension to phase separate.

16 Claims, 3 Drawing Sheets

METHOD AND APPARATUS FOR DETERMINING THE DISPERSION STABILITY OF A LIQUID SUSPENSION

CROSS REFERENCE TO RELATED PATENT APPLICATIONS

This is a non-provisional application of prior pending U.S. provisional application serial No. 60/195,736 filed Apr. 7, 2000.

FIELD OF THE INVENTION

The present invention relates to a method and apparatus for determining the dispersion stability of a liquid suspension containing particles. More particularly, the present invention relates to a method and apparatus for determining the dispersion stability of a liquid suspension through analyzing the light scattering properties of the liquid suspension.

BACKGROUND

A common problem in preparing liquid suspensions containing insoluble particles is that a liquid suspension often becomes unstable and phase separates over time. For example, if the insoluble particles are denser than the liquid, the particles will settle downward, leaving a layer of solids towards the bottom of the suspension, and a liquid layer towards the top of the suspension. In the paint industry, this phase separation phenomenon is sometimes referred to as "syneresis." Dispersion instability, however, is not just limited to paints. For example, dispersion instability often occurs in liquid suspensions such as cosmetic compositions for application to the skin, hair, and nails; topical pharmaceutical compositions; pesticidal or agricultural compositions; mining compositions such as drilling muds; and aqueous or solvent based coatings such as adhesives, polishes, waxes, and coatings for substrates such as wood, reconstituted wood products, concrete, asphalt, fiber cement, stone, marble, clay, plastics, paper, cardboard, leather, textiles, and metal (ferrous as well as non-ferrous). Dispersion instability in these liquid suspensions may be evidenced, for example, by insoluble particles rising to the top of the suspension, or the insoluble particles settling to the bottom of the liquid suspension, depending on the density of the insoluble particles relative to the liquid.

Dispersion instability in a liquid suspension can be caused by a variety of factors. For example, dispersion instability can be caused by not properly dispersing the insoluble particles in the liquid. Dispersion instability can also be caused by subjecting the liquid suspension to external conditions such as shear, heat, or freeze-thaw cycles. Also, dispersion instability can be caused through changes in the particle size of the insoluble particles. For example, additives in the liquid suspension can cause insoluble particles in the liquid suspension to combine together through such mechanisms as bridging flocculation.

A common technique that formulators use for testing the stability of a liquid suspension is to store a sample of the liquid suspension for a predetermined time under predetermined conditions and to visually inspect the sample after the predetermined time to determine if the liquid suspension has phase separated. However, this technique has the disadvantage that it takes time, often more than several hours, to determine whether the liquid suspension is stable. Additionally, the test is subjective in that an operator must visually determine whether phase separation has taken place.

Another technique used for detecting the stability of a liquid dispersion is disclosed in U.S. Pat. No. 5,783,826 to Meunier (hereinafter "Meunier"). Meunier discloses a method and apparatus for analyzing phases of a multi-phase mixture by emitting electromagnetic radiation towards a tube containing the liquid suspension and detecting the radiation back scattered by the liquid dispersion over the length of the tube to detect changes in phases over the length of the tube. Thus, as in a conventional dispersion stability test, actual phase separation must begin to occur for the method and device of Meunier to detect dispersion instability.

The present invention provides a method and apparatus for determining the dispersion stability of liquid suspensions of insoluble particles which does not rely on the liquid suspension actually beginning to phase separate.

STATEMENT OF INVENTION

In one aspect, the present invention provides a method for determining the dispersion stability of a liquid suspension including the steps of providing a liquid suspension comprising insoluble particles; exposing the liquid suspension to a light beam having at least one wavelength of light while maintaining the insoluble particles in the liquid suspension uniformly suspended; determining the quantity of light scattered by the liquid suspension; and analyzing the quantity of light scattered to determine the dispersion stability of the liquid suspension by detecting the presence of modified insoluble particles based on the quantity of light scattered by the liquid suspension.

In another aspect, the present invention provides an apparatus for determining the dispersion stability of a liquid suspension including light generating and detecting equipment for exposing a liquid suspension to a beam of light having one or more wavelengths of light and for determining the quantity of light scattered by the liquid suspension; means for maintaining insoluble particles in the liquid suspension uniformly suspended while exposing the liquid suspension to the beam of light; and an analyzer for analyzing the quantity of light scattered by the liquid suspension at the one or more wavelengths to determine the dispersion stability of the liquid suspension by detecting the presence of modified insoluble particles.

DETAILED DESCRIPTION OF THE INVENTION

Figure 1:
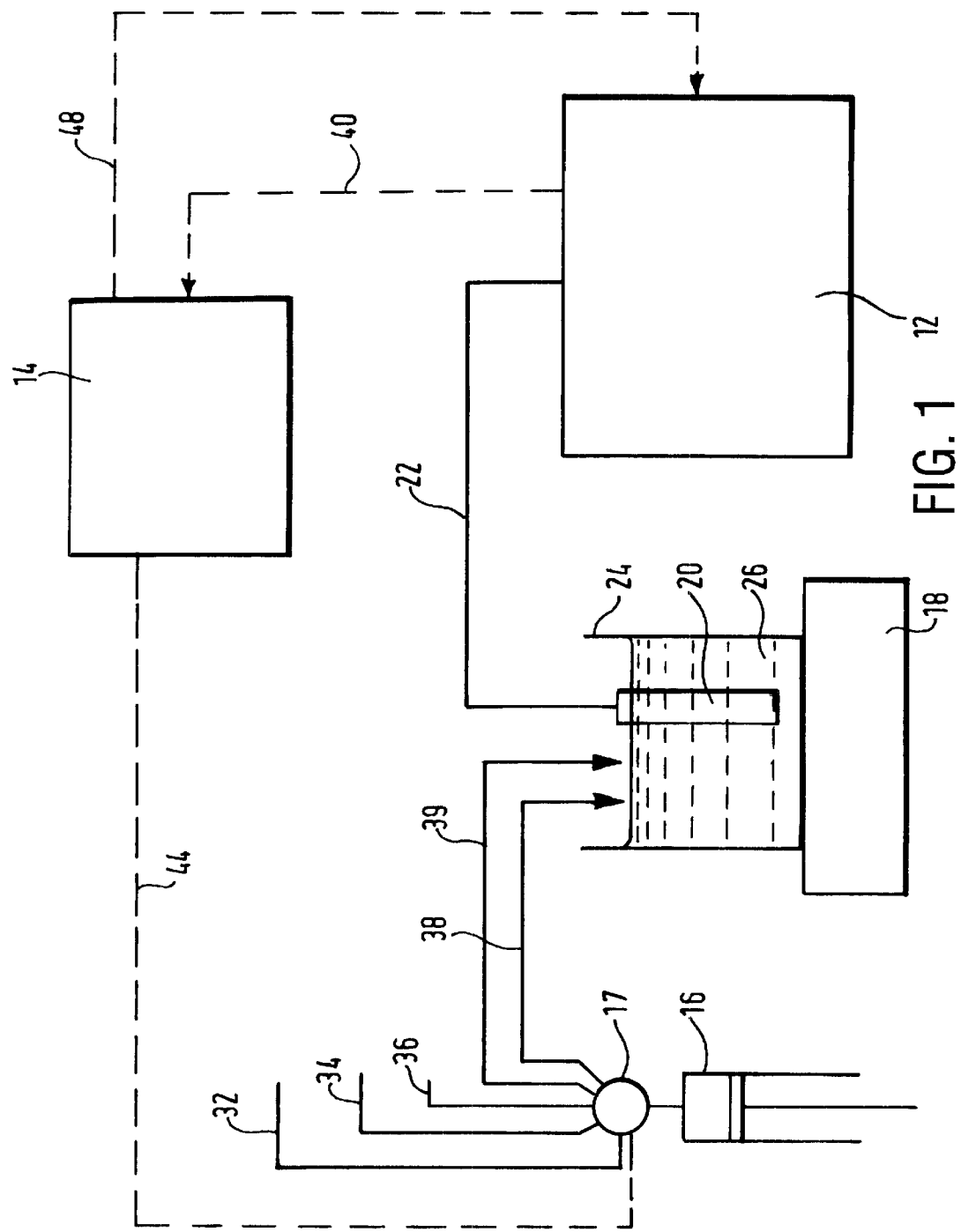
FIG. 1 shows a schematic representation of an embodiment of an apparatus of the present invention.

The present invention provides a method and apparatus for determining the dispersion stability of a liquid suspension containing insoluble particles based on the light scattering properties of the liquid suspension. By "dispersion stability" it is meant the ability of the insoluble particles in the liquid suspension to remain homogeneously dispersed throughout the liquid, without settling, for the desired life of the liquid suspension. The term "insoluble," as used herein, means that the particle remains intact in the suspending medium.

Liquid suspensions that can be analyzed for dispersion stability in accordance with the method and apparatus of the present invention include any liquid suspension that can become unstable due to insoluble particles in the suspension changing in particle size to form a "modified insoluble particle." The term "modified insoluble particle" as used herein means an original insoluble particle that has been modified in some way in the liquid suspension to change its particle size. For example, the modified insoluble particle could be a particle of increased particle size relative to the original insoluble particle. It is also possible, although not as common, that the modified insoluble particle be a particle of decreased particle size, relative to the original insoluble particle. For example, the original insoluble particle can be modified by two more original insoluble particles combining to form a combined particle of increased particle size. This increase in particle size can occur through any mechanism such as flocculation, coagulation, agglomeration, aggregation, coalescence, or combinations thereof. Often combined particles are formed through the presence of an additive, such as a thickener, which causes solid particles in the suspension to combine through such mechanisms as bridging flocculation, depletion flocculation, coagulation or combinations thereof. An increase in particle size can also occur, for example, through precipitation of a soluble ingredient in the liquid suspension onto an insoluble particle. Mechanisms by which the particle size of insoluble particles in the liquid suspension are modified can be reversible or irreversible.

The modified insoluble particles, especially if larger in size relative to the original insoluble particle, have the tendency to separate from or settle out of the liquid to form a distinct phase of solids in the liquid suspension. The term "unstable liquid suspension," as used herein, means that the liquid suspension contains enough modified particles so that dispersion instability is detected (e.g., by observing phase separation over the intended life of the liquid suspension). Typically, an unstable liquid suspension will contain at least about 1 percent to 100 percent modified insoluble particles based on the total number of original insoluble particles in the system. The term "stable liquid suspension," as used herein, means that the liquid suspension does not contain enough modified insoluble particles to visually detect dispersion instability (e.g., typically less than 1% modified insoluble particles based on the total number of original insoluble particles in the system).

Although in no way intending to be bound by theory, it is believed that the present invention is based on the discovery that the change in particle size of particles (especially in the case of particles combining), if it is to occur, happens quickly (e.g., within 30 seconds) after forming the liquid suspension or after adding an additive that causes particles to be modified. However, it takes time for the modified particles to separate and settle from the liquid. Thus, if the modified particles can be detected through other means, one does not have to wait for the modified particles in the liquid suspension to separate from the liquid to determine if the suspension is unstable.

The present invention makes use of the light scattering properties of particles to detect the presence of modified particles in the liquid suspension. The intensity of light scattered by a particle depends, in part, on the diameter of the particle and the wavelength of the light. For example, as the ratio of wavelength to particle size decreases, the amount of scattering increases. Conversely, as the ratio of wavelength to particle size increases, the amount of scattering decreases. Thus, by choosing an appropriate wavelength or wavelengths as described in further detail below, one can observe differences in intensity of light scattering to detect the presence of modified particles.

Preferably, to enhance differences in light scattering between a stable and unstable liquid suspension, the weight average particle diameter of the modified particle differs from the weight average particle diameter of the original particle by at least a factor of 30 and more preferably by at least a factor of 100. For example, where the modified particle is larger than the original particle, preferably the modified particle is at least 30 times greater, and more preferably at least 100 times greater than the weight average particle diameter of the original insoluble particles in the liquid suspension. Also, preferably, the original insoluble particles in the liquid suspension have a weight average diameter of from about 5 nm to about 1000 nm, and more preferably from about 100 nm to about 500 nm. "Weight average particle diameter" as used herein is preferably determined by dynamic light scattering provided that the particles are roughly spherical in shape.

The types of insoluble particles that are present in the liquid suspension will depend upon the type of liquid suspension. Examples of particles that may be present in the liquid suspension include polymer particles used for such purposes as binding agents or opacifying agents; inorganic or organic solid particles such as pigments, fillers, extenders, or any combination thereof. To enhance changes in scattering intensity between a stable and unstable liquid suspension, preferably, the original insoluble particles present in the liquid suspension, contribute less than about 5% and more preferably less than about 3% of the total light scattering of the liquid suspension at wavelengths where one is attempting to detect the presence of modified particles.

As the intensity of light scattered by a liquid suspension is also a function of the number of particles in the suspension, it is also preferable that the liquid suspension have a total level of solid particles that ranges from about 1 wt % to about 50 wt %, more preferably from about 2 wt % to about 20 wt % weight percent, and most preferably from about 5 wt % to about 10 wt % weight percent based on the total weight of the liquid suspension.

Examples of liquid suspensions that can be analyzed in accordance with the methods of the present invention include cosmetic compositions for application to the skin, hair, and nails; topical pharmaceutical compositions; pesticidal or agricultural compositions; mining compositions such as drilling muds; pigment pastes; or aqueous or solvent based coating. Aqueous or solvent based coatings include for example paints (such as latex paints), printing pastes, adhesives, polishes, waxes and other coatings for substrates such as wood, reconstituted wood products, concrete, asphalt, fiber cement, stone, marble, clay, plastics, paper, cardboard, leather, textiles, and metal (ferrous as well as non-ferrous). These compositions may be analyzed in accordance with the methods of the present invention "as is" or diluted to detect the presence of modified particles. Preferably, the compositions are diluted to within the above mentioned weight percent ranges of solids, to reduce the total amount of scattering by the liquid suspension.

In a preferred embodiment of the present invention, the liquid suspension is a liquid coating. Preferably, the liquid coating contains one or more insoluble polymer particles. Preferably, such insoluble polymer particles are latex particles used for example as binders, opacifying agents, or combinations thereof in the liquid suspension. By "latex" it is meant a dispersion of water-insoluble polymer particles which may be prepared by conventional polymerization techniques such as, for example, by emulsion polymerization.

One skilled in the art will recognize that there are many types of the polymer particles that can be used. For example, the polymer particles may be formed from various monomers based on the desired properties of the liquid coating. Useful monomers from which the polymer particles may be formed from include ethylenically unsaturated monomers such as acrylate esters and acids; methacrylate esters and acids; acrylonitrile; methacrylonitrile; acrolein; methacrolein; vinyl aromatic compounds such as styrene, substituted styrene, vinyl pyridine and vinyl naphthalene; vinyl esters of organic acids, such as vinyl acetate; N-vinyl compounds such as N-vinyl pyrrolidone; unsaturated halogenated compounds such as vinyl chloride and vinylidene chloride; acrylamide, methacrylamide and substituted acrylamides and methacrylamides; polymerizable sulfonic acids and salts thereof such as styrene sulfonic acid, sodium vinyl sulfonate, sulfoethyl acrylate, sulfoethyl methacrylate and acryloamidopropanesulfonic acid; vinyl ethers; or combinations thereof.

The polymer particles may also have various morphologies such as in the form of single or multi-staged polymer particles. Multi-staged particles include at least two mutually incompatible copolymers having any number of morphological configurations; for example: core/shell; core/shell particles with shell stages incompletely encapsulating the core; core/shell particles with a multiplicity of cores; interpenetrating network particles, where the greater portion of the surface area of the particles will be occupied by at least one outer stage, and the interior of the particle will be occupied by at least one inner stage. The polymer particles may also contain one or more voids. Such void containing polymer particles are disclosed for example in U.S. Pat. Nos. 3,784,391; 4,798,691; 4,908,271; 4,972,000; published European Patent Application 0,915,108; and Japanese Patent Applications 60/223,873; 61/62510; 61/66710; 61/86941; 62/127336; 62/156387; 01/185311; 02/140272. These void containing polymer particles are particularly useful as opacifying agents.

The concentration of polymer particles in the liquid suspension will depend upon the function of the polymer particles in the liquid suspension. However, preferably, the polymer particles are present in the liquid suspension in an amount of from about 1 weight percent to about 20 weight percent, and more preferably from about 5 weight percent to about 10 weight percent.

Liquid coatings useful in the present invention may also optionally contain additional components including but not limited to: thickeners; rheology modifiers; dyes; sequestering agents; biocides; dispersants; pigments such as titanium dioxide or carbon black; extenders such as calcium carbonate, talc, clays, silicas and silicates; fillers such as glass or polymeric microspheres, quartz, and sand; antifreeze agents; plasticizers; adhesion promoters; coalescents; wetting agents; waxes; surfactants; slip additives; crosslinking agents; defoamers; colorants; preservatives; freeze/thaw protectors; corrosion inhibitors; and alkali or water soluble polymers. Other optional components present in the liquid coating include but are not limited to: co-solvents, reactive pigments, UV absorbers, antioxidants, and stabilizers. These optional components (as desired) may be added in any order of addition which does not cause an incompatibility between components.

In determining the dispersion stability of a liquid suspension, the method of the present invention includes exposing the liquid suspension to a beam of light having at least one wavelength of light while maintaining the insoluble particles in the liquid suspension uniformly suspended and determining the quantity (i.e., intensity) of light scattered. One skilled in the art will recognize that there are various types of light generating and detecting equipment for exposing a liquid suspension to a beam of light and determining the quantity of light scattered. The light generating and detecting equipment is preferably chosen based upon the selection of one or more wavelengths where changes in light scattering between original insoluble particles and modified particles are easily detectable. The light generating and detecting equipment includes a light source, a light detector, and a sample cell for holding the liquid suspension. These components may be purchased individually and assembled as desired by the user, or can be purchased as one unit (e.g., a commercial photometer). Examples of suitable light sources include lasers, arc lamps, flash lamps, or combinations thereof. Examples of light detectors include photodiodes, photomultiplier tubes, or combinations thereof In a preferred embodiment of the present invention, a visible (vis) spectrometer is used.

In exposing the liquid suspension to a beam of light, preferably, the insoluble particles of the liquid suspension (e.g., the original and modified particles) are maintained uniformly suspended. By "uniformly suspended" it is meant that the particles of the liquid suspension are evenly dispersed in the liquid suspension so that no phase separation begins to occur during the analysis. The particles may be maintained in uniform suspension by any manner known to those skilled in the art. For example, any type of mixing equipment known to those skilled in the art may be used. Also, it is possible that the liquid suspension is formulated in such a manner that the particles will remain uniformly suspended while the suspension is being exposed to the beam of light.

The selection of one or more appropriate wavelengths of light for carrying out the method of the present invention will depend on such factors as the weight average diameter of the original and modified insoluble particles, the concentration of insoluble particles in the liquid suspension, the type of light source, the type of detector, and the path length of the sample cell. One skilled in the art, in appreciating these variables, will be able to select an appropriate wavelength where differences in scattering intensity will be observed to determine dispersion stability. Preferably, one or more wavelengths are chosen where light scattering will be different by a factor of at least about 3 for unstable liquid suspensions in comparison to stable liquid suspensions. For example, where the instability in the liquid suspension is caused by the original insoluble particles increasing in size, preferably the wavelength is chosen so that the light scattering will be at least about 3 times greater for an unstable liquid suspension in comparison to a stable liquid suspension.

In a preferred embodiment of the present invention where the modified insoluble particle is larger than the original insoluble particle, the wavelength of light is (a) at least about 3 times and more preferably at least about 5 times greater than the weight average diameter of the original insoluble particles, and (b) at least about 10 times and more preferably at least about 20 times less than the weight average diameter of the modified insoluble particles. For example, for original insoluble particles ranging in size from about 100nm to about 150 nm and modified insoluble particles ranging in size from about 10 microns to about 100 microns, preferably the wavelength of light is from about 375 nm to about 1000 nm and more preferably from about 625 nm to about 950 nm.

In a preferred embodiment of the present invention, the light beam contains a plurality of wavelengths of light so that a spectrum can be obtained showing changes in light scattering for a liquid suspension over a range of wavelengths. When more than one wavelength is used, preferably the range of wavelengths that the liquid suspension is exposed to is chosen such that the smallest wavelength ranges from about 3 to about 5 times the weight average particle diameter of the original insoluble particle, and the greatest wavelength ranges from about 0.01 to about 0.1 times the weight average particle diameter of the modified insoluble particle. For a liquid suspension having original insoluble particles ranging in weight average diameter from about 100 nm to about 150 nm, preferably the liquid suspension is exposed to a light beam having the smallest wavelength ranging from about 375 nm to about 625 nm and the greatest wavelength ranging from about 950 nm to about 1000 nm.

One skilled in the art will recognize that there are also other parameters when using light generating and detecting equipment that can be adjusted to enhance changes in light scattering to detect the presence of dispersion instabiliy of a liquid suspension. Such parameters include for example, path length of the cell, lamp intensity, detector sensitivity, integration time, angle of collection, and the selection of a blank solution used for comparison against the liquid suspension in obtaining a spectrum for the liquid suspension. One skilled in the art will know how to adjust such parameters to detect varying particle sizes in different liquid suspensions. For example, if an increased cell path length is desired, integrating the signal for a longer period of time can correct the poorer signal to noise ratio generated due to increased scattering by the longer cell path length.

The method by which the quantity of light scattered is determined will depend upon such factors as the type of light generating and detecting equipment selected and the angular distribution of the intensity. For example, the amount of light scattering can be determined through measuring the amount of light transmitted through the liquid suspension. This amount can be expressed in either transmittance units or absorbance units. When expressed in transmittance units, the values will decrease as scattering increases. When expressed in absorbance units, the values will increase as scattering increases. Alternatively, the scattered light can be measured directly by placing the light detecting equipment off the axis of the incident light beam, thus collecting the light scattered at a specific angle or range of angles. Also, the total scattered light can be collected by using optics that collect the light scattered at all angles.

In a preferred embodiment of the present invention, light scattering is determined by measuring the amount of light transmitted through the sample cell holding the liquid suspension in a direction equal to the direction of illumination. Preferably the light transmitted is expressed in absorbance units. Also, preferably, the liquid suspension is evaluated for light scattering properties within about 60 minutes, more preferably within about 15 minutes and most preferably within 1 minute after preparing the liquid suspension. By performing the evaluation within the aforementioned time frame, one does not have to wait for extended periods of time to observe any phase separation of the liquid suspension that may occur.

The quantity of light scattered by the liquid suspension is then analyzed to determine the dispersion stability of the liquid suspension. The analysis is preferably performed by obtaining values for the quantity of light scattered (e.g., light absorbance and/or light transmittance values) by a liquid suspension at one or more appropriate wavelengths to detect the presence of modified insoluble particles. For example, in the case of modified insoluble particles that are larger than the original insoluble particles, by exposing a liquid suspension to a wavelength of light where the wavelength of light is much greater than the weight average diameter of the original insoluble particle (e.g., preferably at least 3 times greater than the weight average diameter of the original insoluble particle), and preferably at least 5 times less than the weight average particle diameter of the modified insoluble particle, much less scattering will be observed for a liquid suspension containing original insoluble particles (e.g., a stable liquid suspension) in comparison to a liquid suspension containing modified insoluble particles (e.g., an unstable liquid suspension). Thus, one can tell, based on one or more light scattering values at one or more appropriate wavelengths whether the liquid suspension contains modified insoluble particles and as a result may have dispersion instability.

In a preferred embodiment of the present invention, the analysis preferably includes determining at least one characteristic value derived from the quantity of light scattered at one or more wavelengths by the liquid suspension and comparing the characteristic value to at least one threshold value. The "characteristic value" as used herein is any value that quantifies the intensity of light scattering for a liquid suspension and that can be used to determine whether the liquid suspension contains modified insoluble particles. For example, the characteristic value can be the light absorbance or light transmittance at a wavelength where the light scattering will be at least about 3 times greater for an unstable liquid suspension in comparison to a stable liquid suspension (assuming the modified insoluble particles are larger than the original insoluble particles). The characteristic value could also be obtained from computing a value from two or more absorbance values or two or more transmittance values at predetermined wavelengths to distinguish a liquid suspension containing modified insoluble particles from a liquid suspension containing original insoluble particles. The "threshold value" as used herein is a value determined in the same manner as the characteristic value for a liquid suspension that knowingly is a stable liquid suspension or an unstable liquid suspension (contains modified insoluble particles in an amount rendering the liquid suspension unstable). Thus, the threshold value quantitatively identifies the light scattering properties of a "control liquid suspension" (i.e., a suspension where the stability or instability is known) that is compared to the light scattering properties of a liquid suspension that is being analyzed for dispersion stability.

The method of the present invention can be used in any application where it is desired to determine the presence of modified insoluble particles in a liquid suspension for the purposes of determining dispersion stability. For example, any liquid suspension where insoluble particles have the tendency to combine through such mechanisms as flocculation, coagulation, agglomeration, aggregation or combinations thereof can use the method of the present invention to detect dispersion stability. It is also contemplated that the method of the present invention can be used to predict the stability of liquid suspensions having higher concentrations of solids by determining the light scattering properties of the same liquid suspension, but diluted to provide a lower concentration of solids.

In a preferred embodiment of the present invention, the method of the present invention can be used to assess the quality of at least one additive, or to determine one or more amounts of the at least one additive that can cause dispersion instability in a liquid suspension, or combinations thereof. Preferably, the additive that is evaluated is soluble or partially soluble in the liquid dispersion so that it contributes an insignificant amount of light scattering in comparison to the insoluble particles in the liquid suspension (e.g., less than about 5% of the total light scattering of the liquid suspension). Examples of additives include thickeners or rheology modifiers, defoamers, coalescents, wetting agents, colorants, preservatives, freeze/thaw protectors, corrosion inhibitors, or combinations thereof.

In a preferred embodiment of the method of the present invention, the quality of the additive or the amount of additive causing dispersion instability is determined by adding the additive to the liquid suspension in one or more additions and evaluating the liquid suspension for light scattering properties after one or more of the additions. Preferably, the liquid suspension is evaluated for light scattering properties after each addition of additive. For example, after each addition of additive, preferably, the liquid suspension is exposed to a beam of light and the quantity of light scattered by the liquid suspension is determined and analyzed in accordance with the methods previously described herein. Preferably, the liquid suspension is evaluated for light scattering properties within about 1 minute, and more preferably within about 30 seconds after adding the additive to the liquid suspension. The resulting analysis can provide one information regarding amounts of an additive that can be added without causing dispersion instability. The analysis can also provide information related to the quality of an additive. For example, when the quality of the additive affects dispersion stability, the additive can be added in one or more amounts to determine at what amount, if any, dispersion instability arises in the liquid suspension.

An advantage to using the method of the present invention in evaluating the effect of an additive in a liquid suspension is that one can obtain dispersion stability information without waiting for the liquid suspension to settle in accordance with conventional test methods. This allows one to more quickly develop suitable formulations of liquid suspension.

In a preferred embodiment of the present invention the additive that is evaluated is one or more thickeners. The term "thickener" as used herein is any additive which modifies the rheology properties of a liquid suspension and includes rheology modifiers. Thickeners are known to cause dispersion instability problems in liquid suspensions such as latex paints. For example, thickeners often "bridge" or connect latex polymer particles together to form a modified insoluble particle of larger size. These modified insoluble particles then over time settle and cause syneresis in the paint.

Thickeners that can be evaluated in accordance with the method of the present invention include nonionic or anionic, water soluble or water swellable polymers. Useful thickeners also include associative or nonassociative thickeners. "Associative thickeners" are water soluble or water swellable polymers that have chemically attached hydrophobic groups which are capable of hydrophobic associations. The attached "hydrophobic groups" are typically any chemical group which promotes water insolubility such as alkyl or alkaryl groups containing from about 4 to about 30 carbon atoms. "Nonassociative thickeners" are water soluble or water swellable polymers that do not have chemically attached hydrophobic groups.

One skilled in the art will recognize that there are various thickeners that can be evaluated in accordance with the methods of the present invention. Examples of thickeners include polyethoxylated urethanes, such as those described in U.S. Pat. Nos. 4,079,028 and 4,155,892, the disclosures of which are hereby incorporated by reference in their entireties. Such polyethoxylated urethanes include condensation polymers of polyether polyols and isocyanates. Other useful thickeners include acrylic carboxylate emulsion polymers. Acrylic carboxylate emulsion polymers preferably are formed from at least one monoethylenically unsaturated carboxylic acid, at least one $C_1$ to $C_4$ alkyl acrylate or alkyl methacrylate, and optionally at least one acrylic or methacrylic acid ester of an ethoxylated hydrocarbyl alcohol. The thickener may also be an acrylamide containing polymer formed from at least one acrylamide or N-substituted acrylamide monomer. In a preferred embodiment of the present invention, the thickener is one or more polyethoxylated urethanes. For example, the method of the present invention may be used to assess the quality of one or more polyethoxylated urethanes or may be used to determine amounts at which a polyethoxylated urethanes will cause a liquid suspension to have dispersion instability.

In another aspect of the present invention, an apparatus is provided for determining the dispersion stability of a liquid suspension. The apparatus includes light generating and detecting equipment for exposing a liquid suspension to a beam of light having one or more wavelengths of light, and for determining the quantity of light scattered by the liquid suspension; means for maintaining insoluble particles in the liquid suspension uniformly suspended while exposing the liquid suspension to the beam of light; and an analyzer for analyzing the quantity of light scattered by the liquid suspension to determine the dispersion stability of the liquid suspension.

The light generating and detecting equipment may be any apparatus capable of generating and exposing a liquid suspension to a beam of light having one or more wavelengths, and determining the amount of light that is scattered by the liquid suspension. One skilled in the art will recognize that there are various types of light generating and detecting equipment for exposing a liquid suspension to a beam of light and determining the quantity of light scattered. The light generating and detecting equipment is preferably chosen based upon the selection of one or more wavelengths where changes in light scattering between original insoluble particles and modified particles are easily detectable. The light generating and detecting equipment as previously described includes a light source, a light detector, and a sample cell for holding the liquid suspension. These components may be purchased individually and assembled as desired by the user, or can be purchased as one unit (e.g., a commercial photometer). In a preferred embodiment of the present invention, the light generating and detecting equipment is a visible (vis) spectrometer.

The apparatus of the present invention also includes means for maintaining insoluble particles uniformly suspended in the liquid suspension while exposing the liquid suspension to the beam of light. Any type of equipment that is effective in maintaining the insoluble particles uniformly suspended may be used. Examples of equipment include various types of mixing equipment such as for example, magnetic stirrers, static mixers, motor or air driven mixer blades, shakers, sonicators, or combinations thereof. The means for maintaining the insoluble particles suspended may also be the manner in which the liquid suspension is temporarily formulated so the particles remain uniformly suspended while the suspension is being exposed to the beam of light.

The analyzer useful in the apparatus of the present invention is any device capable of receiving values for the quantity of light scattered at one or more wavelengths (e.g., light absorbance or light transmittance), and determining the dispersion stability of liquid suspension based on the values received. Preferably, the analyzer receives one or more values for light scattering (e.g., light absorbance and/or light transmittance values) of a liquid suspension at one or more appropriate wavelengths to detect the presence of modified insoluble particles. Where the modified insoluble particles are larger than the original insoluble particles, an appropriate wavelength would be for example where the wavelength of light is much greater than the weight average diameter of the original insoluble particle (e.g. at least about 3 times greater than the weight average diameter of the original insoluble particle), and at least about 5 times less than the weight average particle diameter of the modified insoluble particle. Although such an analysis could be performed manually by a person, preferably the analyzer is a computer having a computer-readable medium, such as a computer program, that performs the analysis.

In a preferred embodiment of the present invention, the analyzer includes a computer-readable medium containing computer-implement-able instructions for receiving from the light generating and detecting equipment values for the quantity of light scattered by the liquid suspension at one or more wavelengths; calculating at least one characteristic value based on the quantity of light scattered at the one or more wavelengths; and comparing the characteristic value to at least one threshold value to determine the presence of modified insoluble particles in the liquid suspension. The characteristic value, as previously described herein, is any value that quantifies the amount of light scattering for a liquid suspension and that can be used to determine whether the liquid suspension contains modified insoluble particles. The threshold value as previously described herein is a value determined in the same manner as the characteristic value for a control liquid suspension (i.e., a liquid suspension of known stability).

A preferred embodiment of an apparatus of the present invention will now be described with reference to FIG. 1. FIG. 1 shows a schematic representation of a preferred apparatus 10 of the present invention for determining the dispersion stability of a liquid suspension. The apparatus 10 is fully automated and includes a spectrometer 12, a computer 14, a digital syringe pump 16, and a magnetic stirrer 18.

The spectrometer 12 is a photometer having a fiber optic probe 20 and a fiber optic cable 22. The probe 20, when in use, is disposed within a container 24 of liquid suspension 26. The probe 20 has a sample cell (not shown), that when immersed in the liquid suspension 26, is filled with liquid suspension 26. The probe 20 receives from the spectrometer 12 a beam of light (not shown) via the fiber optic cable 22, and exposes the liquid suspension 26 in the sample cell to the beam of light. The probe 20 also transmits the amount of unscattered light from the liquid suspension 26 in the sample cell to the spectrometer via the fiber optic cable 22. The spectrometer 12 detects the amount of unscattered light received from the fiber optic cable 22, and determines the quantity of light scattered by the liquid suspension 26 based on the amount of light detected. The spectrometer also communicates values for the quantity of light scattered at each wavelength to computer 14 via path 40 for analysis. The computer 14 contains a computer program (not shown) as previously described herein for determining the dispersion stability of the liquid suspension 26.

In a preferred embodiment of the present invention, the apparatus includes feeding equipment for feeding at least one additive to the liquid suspension. This feeding equipment can also be used to prepare the initial liquid suspension as described in more detail hereinafter. One skilled in the art will recognize numerous ways to feed a controlled amount of additive to the liquid suspension. For example, pumps alone, or in combination with one or more valves can be used to feed additive. Additionally, additives can be fed by gravity or by pressure differences if used with a valve or other mechanism to stop the feed after the desired amount of additive has been added.

In FIG. 1, the feeding equipment is a digital syringe pump 16. The digital syringe pump 16 has a multiport valve 17 for feeding one or more ingredients into container 24 via lines 38 and 39. For example, in FIG. 1, lines are provided for feeding water from line 32, an aqueous dispersion of latex polymer particles from line 34, and an additive such as a thickener from line 36.

Preferably as shown in FIG. 1, the apparatus is fully automated through the use of computer 14. The computer in FIG. 1 not only analyzes the data received from the spectrometer 12 via path 40 to determine dispersion stability, but also controls the operation of the spectrometer via path 48 and the feeding equipment via path 44. For example, in FIG. 1, the computer 14 commands the digital syringe pump to add water, latex, or additive via path 44. Computer 14 also commands the spectrometer 12 to determine the light scattering properties of the liquid suspension at the desired times via path 48.

Preferably, computer 14 analyzes the light scattering data from the spectrometer 12, and controls the spectrometer 12 and feeding equipment through the use of a computer readable medium such as a computer program. The computer program, in addition to analyzing the data from the spectrometer, preferably has instructions for coordinating the operation of the spectrometer and the feeding equipment. For example, the computer program preferably has instructions for commanding the feeding equipment to add additive to the liquid suspension, and commanding the light generating and detecting equipment to expose the liquid suspension to the beam of light and to determine the light scattered by the liquid suspension after one or more additions of the additive. The computer program also preferably has instructions for preparing the starting liquid suspension. For example, the computer program preferably has instructions for the digital syringe to add to the container 24 a desired amount of latex from line 34 and water from line 32 to prepare the starting liquid suspension.

One skilled in the art will recognize that there are various other ways in addition to FIG. 1 to design the apparatus of the present invention to determine the dispersion stability of a liquid suspension. For example, although FIG. 1 shows one computer, one skilled in the art will recognize that more than one computer could be used to control the equipment and analyze the data obtained from the spectrometer. Also, for example, the computer program can be tailored to meet the specific needs of the user.

EXAMPLES

Some embodiments of the invention will now be described in detail in the following Examples.

Example 1

The quality of a rheology modifier was assessed using the method of the present invention. The apparatus included a Hewlett-Packard Model 8453 UV/Vis spectrometer equipped with a 0.2 cm path length cell.

The rheology modifier tested in this example was a polyethoxylated urethane formed from the condensation reaction of polyethylene glycol monoether having a molecular weight of 8000 and 4,4 biscylohexylmethane diisocyanate. The polyethoxylate urethane was capped at the ends with n-hexanol. Prior to use, the rheology modifier was diluted with deionized water to provide a rheology modifier solution having 0.3 weight percent polymer based on the total weight of the solution.

Six liquid suspensions were prepared containing acrylic latex polymer and the rheology modifier. The acrylic latex polymer had a weight average particle size of 125 nm as measured by dynamic light scattering. Each sample contained 7.7 weight percent latex polymer based on the total suspension weight. The suspensions contained 0.4%, 0.5%, 0.6%, 0.7%, 0.8% and 0.9% dry weight of rheology modifier based on total dry weight of latex polymer. Each vial contained approximately 6 ml of suspension.

Figure 2:
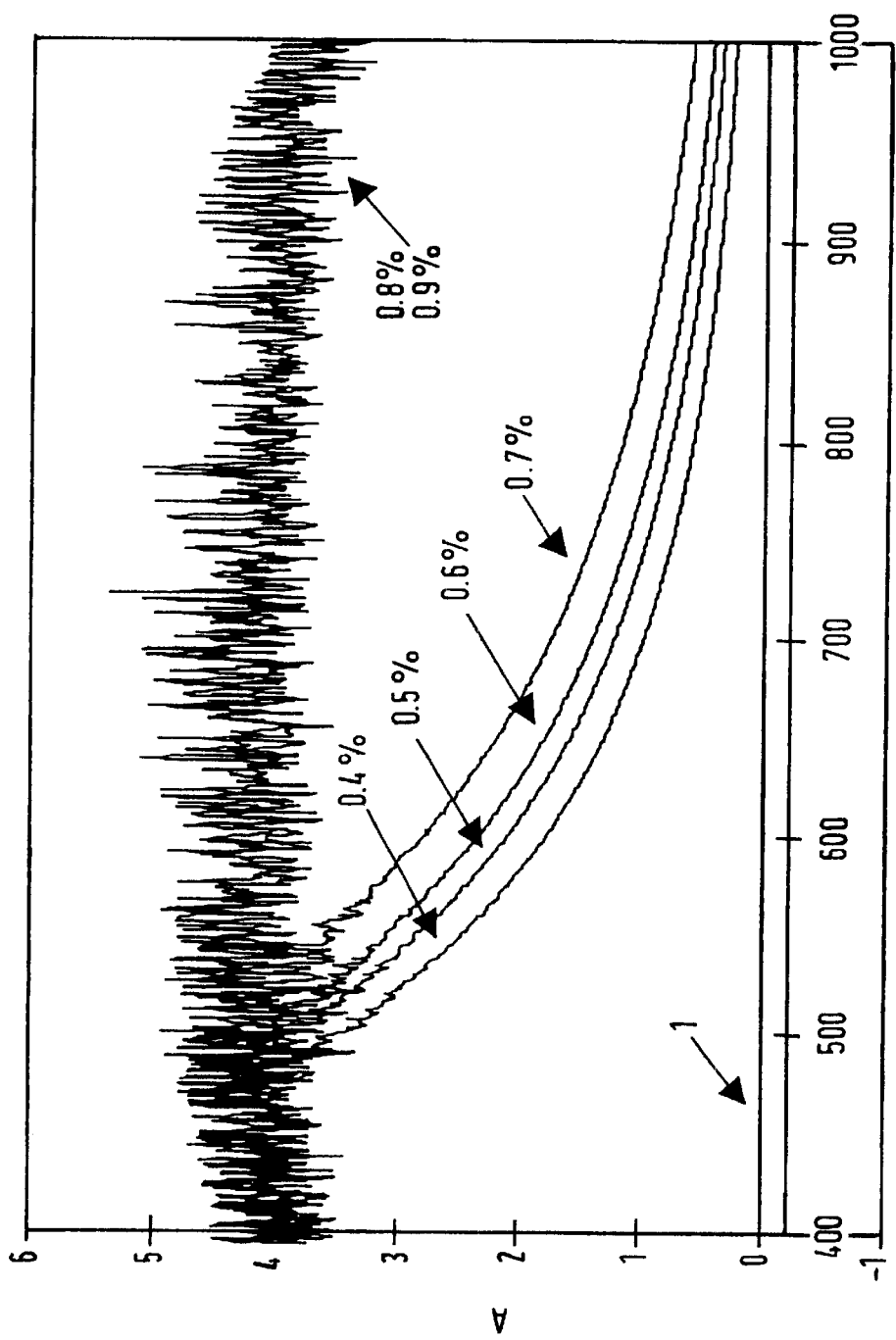
FIG. 2 shows the scattered light expressed as absorbance units (axis marked "A") versus wavelength of light in nanometers (axis marked "W") for liquid suspensions containing various levels of a rheology modifier. The blank spectrum was pure water.

Each of the liquid suspensions were then evaluated for light scattering properties using the spectrometer. The light absorbance data obtained for each suspension is shown in FIG. 2. FIG. 2 shows the relationship of light absorption in absorbance units (axis marked "A") versus wavelength in nanometers (axis marked "W") for the liquid suspensions having concentrations of rheology modifier ranging from 0.4% to 0.9% weight based on the total weight of dry latex polymer. In obtaining the spectra in FIG. 2 for the liquid suspensions, water was used as the blank (Line 1, on FIG. 2).

The light absorption data in FIG. 2 show that as the level of rheology modifier is increased from 0.4% to 0.7%, there is a slight increase in absorbance, resulting from a slight increase in scattering as insignificant amounts of modified particles are formed. At 0.8% weight rheology modifier, the absorbance value increases dramatically, reaching the maximum that the spectometer is capable of measuring. This increase is the result of a dramatic increase in the intensity of scattered light. For example, at 850 nm, the 0.7% sample has an absorbance of approximately 1 and the 0.8% sample has an absorbance of approximately 4. This represents a 1000-fold decrease in the amount of light transmitted through the sample as a result of the increased scattering.

The six liquid suspensions prepared above were also tested for stability using a conventional storage stability test. Approximately 6 milliliters of liquid suspensions were stored in 0.5 oz vials for 24 hours at room temperature. Following the 24 hour storage period, the liquid suspensions were evaluated for the presence of a particle layer towards the bottom of the liquid suspension. The results of the evaluation are reported below in Table 1. A "fail" indicates that at least a 0.2 ml particle layer was observed and the suspension is unstable. A pass indicates that no such particle layer was observed and the suspension is stable.

TABLE 1

Storage Stability of Liquid Suspensions

| Composition of Suspension | Weight % Rheology Modifier | Absorbance at 850 nm (Absorbance Units) | Storage Stability |
|---|---|---|---|
| A | 0.4 | ~0.5 | pass |
| C | 0.5 | ~0.6 | pass |
| D | 0.6 | ~0.7 | pass |
| E | 0.7 | ~1.0 | pass |
| F | 0.8 | ~4.0 | fail |
| G | 0.9 | ~4.0 | fail |

As can be seen from Table 1 above, light scattering properties of the liquid suspension (reported in absorbance units at 850 nm in Table 1) can be used to determine dispersion stability of a liquid suspension. For example, liquid suspensions in Table 1 having a rheology modifier concentration of 0.8% or greater, were determined to be unstable using a conventional storage stability test and using the method of the present invention (as shown by the significant increase in absorbance at rheology modifier concentrations of 0.8% or greater).

Example 2

The quality of a rheology modifier was assessed using the method and apparatus of the present invention. The apparatus included (a) a Spectral Instruments Model 440 Vis spectrometer having a 0.5 cm path length fiber optic probe, supplied by Spectral Instruments located in Tucson, Az., (b) a Kloen Model 50300 Digital Syringe Pump equipped with an 8-port valve, 10 ml syringe and 48000 step option, supplied by Kloehn, Inc. located in Las Vegas, Nev., and (c) a Pentium computer having 2 serial ports, supplied by Compaq Computer Corp. located in Houston, Tex. The spectrometer, digital syringe, and computer were configured with a magnetic stirrer as shown in FIG. 1. The spectrometer was further set up by adjusting the lamp shutter so that an aqueous solution containing 1 weight percent acrylic latex polymer would scatter light at an intensity of 4500 units as measured by the Spectral Instruments Control Software. The acrylic latex polymer and rheology modifier used in this example were the same as that used in Example 1. Prior to use, the rheology modifier was diluted with deionized water to provide a rheology modifier solution having 0.3 weight percent polymer based on the total weight of the solution.

An enclosable jar containing a magnetic stir bar was placed on the magnetic stirrer. The enclosable jar had a lid with a 0.030" and a 0.020" feeding line connected to the syringe as shown in FIG. 1. To form the liquid suspension, 2.08 mls of the acrylic latex polymer, that was diluted with deionized water to contain 12% polymer solids, was added to the jar with the digital syringe with stirring. Following addition of the latex polymer, 22.92 mls of deionized water was added to the jar by the digital syringe to provide a total level of latex solids of 1.0% weight percent based on the total weight of the liquid suspension.

The liquid suspension was then exposed to a light beam having wavelengths ranging from 650 nm to 950 nm, and the amount of light absorbed was determined by the spectrometer at each wavelength of light. This spectrum is the "blank" spectrum used to determine the absorbance spectrum of subsequent samples.

Following this initial measurement, the rheology modifier, prepared as described above, was added, with mixing, in an amount to provide a concentration of rheology modifier in the liquid suspension of 0.400 wt % based on the total weight of dry latex polymer. Following 0.5 minutes of mixing, the liquid suspension was again exposed to a beam of light ranging in wavelength from 650 nm to 950 nm and the amount of light absorbed by the liquid suspension was determined. This procedure of adding the rheology modifier and measuring the light absorbance of the liquid suspension was repeated again, except that the amount of rheology modifier added was in an amount to increase the concentration of rheology modifier in the liquid suspension by 0.050 wt % (i.e., to a concentration of 0.450 wt % rheology modifier). This procedure was repeated, except the rheology modifier was added in increments to provide liquid suspensions having rheology modifier concentrations shown below in Table 2, and performing light absorbance measurements after each addition of rheology modifier.

Figure 3:
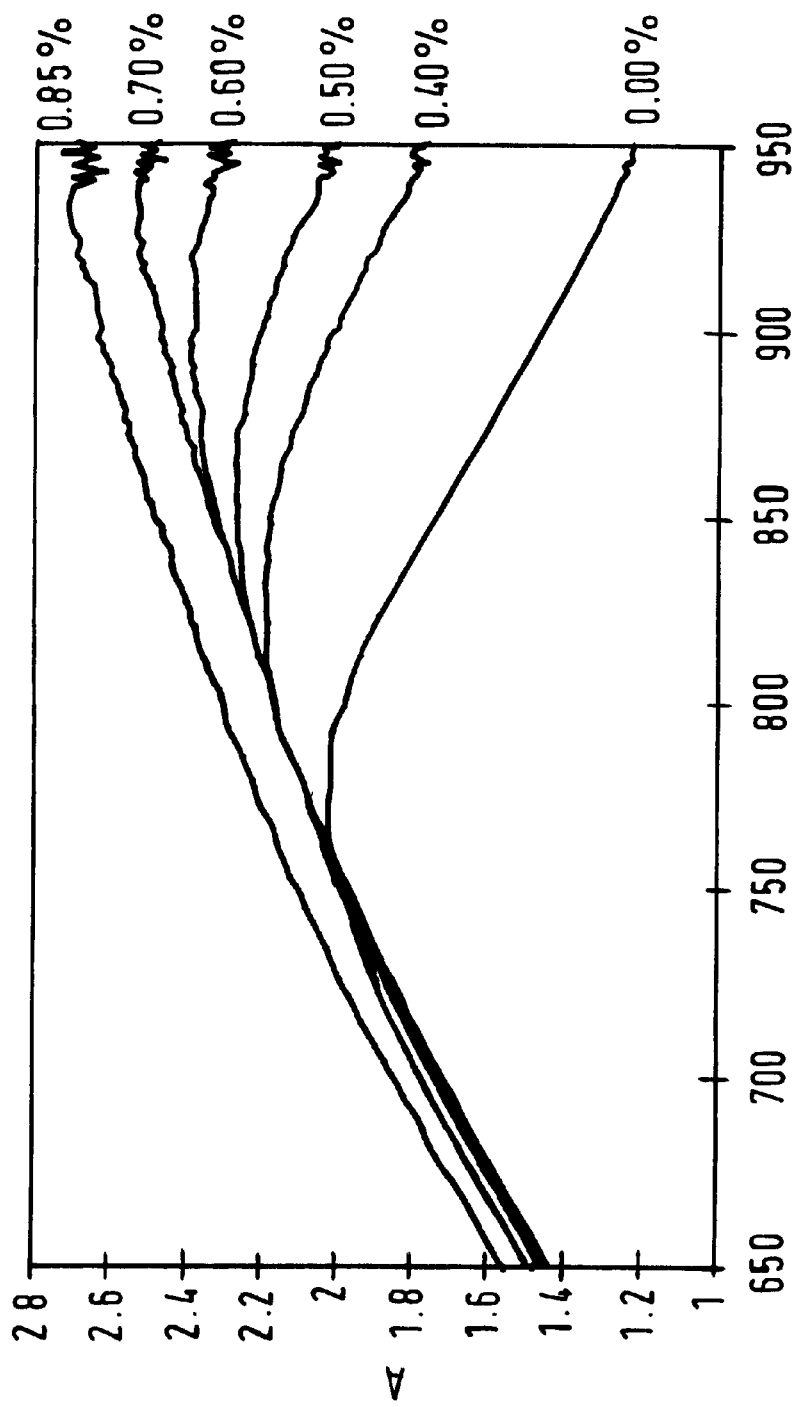
FIG. 3 shows the scattered light expressed as absorbance units (axis marked "A") versus wavelength of light in nanometers (axis marked "W") for liquid suspensions containing various levels of a rheology modifier. The blank spectrum was a 1% acrylic latex suspension.

The light absorbance data obtained by the above method is shown in FIG. 3. FIG. 3 shows the relationship of light absorption in Absorbance Units (axis marked "A") versus wavelength in nanometers (axis marked W) for the liquid suspension having concentrations of rheology modifier ranging from 0 weight percent to 0.85 weight percent based on the total weight of the dry latex polymer. For rheology modifier concentrations ranging from 0 percent to 0.6 percent the light absorbance of the liquid suspension begins to decrease at around 800 nm. For example, at 0.0 wt % added rheology modifier, there are no modified particles present and the dispersion is stable. Also at 0.0 wt % added rheology modifier, the decrease in absorbance above about 800 nm is due to the ratio of the wavelength of the light to the particle diameter becoming larger, and thus having less scattered light, and therefore less absorbance. One skilled in the art will recognize that the curved shape of the absorbance spectrum at 0.0 wt % rheology modifier is a consequence of having used a 1 wt % latex suspension as the "blank" spectrum.

As rheology modifier is added to reach the 0.40 wt % level, some very small fraction of the particles increase in particle size due to the particles combining. This increases the weight average particle diameter and decreases the ratio of wavelength to particle diameter at any given wavelength. As this ratio decreases, the amount of light scattered increases, which leads to an increased absorbance at a given wavelength. As more rheology modifier is added, more particles combine, leading, by the same process, to an ever increasing absorbance at a given wavelength.

From the light absorbing data in FIG. 3, a characteristic value was calculated. This value was calculated by: (a) setting a counter to zero; (b) at a Wavelength (W) of 650 nm, subtracting the absorbance at W+15 (e.g., 665 nm) from that at W (e.g., 650 nm); (c) if the difference in step (b) is negative, adding one to the counter;(d) increasing W by 1 nm, and (e) if W is 935nm, ending the calculation, or if W is less than 935 going to step (b) and repeating steps (b) through (c). At the end of the calculation, the characteristic value is set equal to the counter.

As can be seen from the above calculation, the characteristic value detects the downward sloping section of the curve beginning at around 800 nm. For example, as this downward sloping section becomes smaller, the characteristic value decreases, indicating increased light scattering and an increase in the presence of modified particles formed through particle combination.

The characteristic values obtained are reported below in Table 1. For this particular liquid suspension, when the characteristic value is greater than 10 (e.g., the threshold value), it indicates the absence of significant numbers of modified particles in the liquid suspension. When the characteristic value is less than 10 it indicates that the liquid suspension does contain significant numbers of modified insoluble particles.

To demonstrate that changes in scattering intensity relate to dispersion stability, liquid suspensions were prepared containing 7.0 weight percent of the acrylic latex polymer and the rheology modifier ranging in concentration from 0 weight percent to 1.0 weight percent based on the total dry weight of latex. These liquid suspensions were of the same composition as the liquid suspensions analyzed above for light scattering properties. The liquid suspensions were then stored in 0.5 oz vials for 24 hours at room temperature. Each vial contained about 6 ml of liquid suspension.

Following the 24 hour storage period, the liquid suspensions were evaluated for the presence of a solid layer towards the bottom of the liquid suspension. The results of the evaluation are reported below in Table 2. A "fail" indicates that at least a 0.2ml particle layer was observed and the suspension is unstable. A "pass" indicates that no such particle layer was observed and the suspension is stable.

TABLE 2

Storage Stability of Liquid Suspensions

| Composition of Suspension | Weight % Rheology Modifier | Characteristic Value | Storage Stability |
|---|---|---|---|
| A | 0.0 | 141 | pass |
| B | 0.4 | 89 | pass |
| C | 0.5 | 64 | pass |
| D | 0.6 | 31 | pass |
| E | 0.7 | 0 | fail |
| F | 0.85 | 0 | fail |
| G | 0.95 | 0 | fail |

As can be seen from Table 2 above, the characteristic value, indicating whether modified insoluble particles are present in a liquid suspension correlates with the dispersion stability obtained by a conventional storage stability test. For example, liquid suspensions in Table 1 having a rheology modifier concentration of 0.7% or greater, were determined to be unstable using a conventional storage stability test and using the method of the present invention.

What is claimed is:

1. A method for determining the dispersion stability of a liquid suspension comprising:

(a) providing a liquid suspension comprising insoluble particles;

(b) exposing the liquid suspension to a light beam having at least one wavelength of light while maintaining the insoluble particles in the liquid suspension uniformly suspended;

(c) determining the quantity of light scattered by the liquid suspension; and (d) analyzing the quantity of light scattered to determine the dispersion stability of the liquid suspension by detecting the presence of modified insoluble particles based on the quantity of light scattered by the liquid suspension.

2. The method of claim 1, wherein the liquid suspension is a liquid coating.

3. The method of claim 1, wherein the modified particles have a weight average particle diameter that is at least 30 times greater than the weight average particle diameter of the insoluble particles in the liquid suspension.

4. The method of claim 3, wherein the wavelength of light is at least 3 times greater than the weight average diameter of the insoluble particles and at least 10 times less than the weight average diameter of the modified particles.

5. The method of claim 4, wherein the light beam contains a plurality of light wavelengths.

6. The method of claim 5, wherein the analyzing comprises determining at least one characteristic value obtained from the quantity of light scattered at one or more wavelengths and comparing the characteristic value to at least one threshold value.

7. The method of claim 1, further comprising assessing the quality of an additive or determining an amount of the additive that can cause dispersion instability in the liquid suspension, or combinations thereof.

8. The method of claim 7 further comprising adding one or more quantities of the additive to the liquid suspension; exposing the liquid suspension to the beam of light after one or more of the additions of the additive, and determining the quantity of light scattered by the liquid suspension.

9. The method of claim 8 wherein the additive is a thickener.

10. An apparatus for determining the dispersion stability of a liquid suspension comprising:
   (a) light generating and detecting equipment for exposing a liquid suspension to a beam of light having one or more wavelengths of light and for determining the quantity of light scattered by the liquid suspension;
   (b) means for maintaining insoluble particles in the liquid suspension uniformly suspended while exposing the liquid suspension to the beam of light; and
   (c) an analyzer for analyzing the quantity of light scattered by the liquid suspension at the one or more wavelengths to determine the dispersion stability of the liquid suspension by detecting the presence of modified insoluble particles.

11. The apparatus of claim 10, wherein the analyzer comprises a computer-readable medium having computer-implement-able instructions thereon for performing the steps comprising:
   (i) receiving from the light generating and detecting equipment the quantity of light scattered by the liquid suspension at the one or more wavelengths;
   (ii) calculating at least one characteristic value based on the quantity of light scattered at the one or more wavelengths; and
   (iii) comparing the characteristic value to at least one threshold value to determine the presence of modified particles in the liquid suspension.

12. The apparatus of claim 11 further comprising feeding equipment for feeding at least one additive to the liquid suspension.

13. The apparatus of claim 12 wherein the computer-readable medium further comprises computer-implement-able instructions thereon for performing the steps comprising:
   (iv) commanding the feeding equipment to add additive to the liquid suspension; and
   (v) commanding the light generating and detecting equipment to expose the liquid suspension to the beam of light and to determine the quantity of light scattered by the liquid suspension after the one or more additions of the additive.

14. The apparatus of claim 13 wherein the analyzer further comprises a computer for controlling the light generating and detecting equipment, and feeding equipment; and for executing the computer-implement-able instructions of the computer readable medium.

15. The apparatus of claim 14 wherein the light generating and detecting equipment comprises a photometer.

16. The apparatus of claim 15 wherein the photometer comprises a probe for exposing the liquid suspension to the beam of light and for receiving unscattered light from the liquid suspension, and a fiber optic cable for transmitting the beam of light to the probe and for transmitting the unscattered light from the probe to the photometer.

* * * * *